United States Patent [19]

Herman et al.

[11] Patent Number: 4,801,744

[45] Date of Patent: Jan. 31, 1989

[54] CATALYTIC SYNTHESIS OF UREA FROM CARBON MONOXIDE AND AMINE COMPOUND

[75] Inventors: Jean-Jacques Herman, Waterloo; André Lecloux, Meise, both of Belgium

[73] Assignee: Solvay & Cie (Societe Anonyme), Brussels, Belgium

[21] Appl. No.: 834,504

[22] Filed: Feb. 28, 1986

[30] Foreign Application Priority Data

Mar. 1, 1985 [FR] France .................................. 85 03175

[51] Int. Cl.$^4$ ........................................... C07C 126/00
[52] U.S. Cl. ...................................... 564/65; 528/422; 560/24; 564/55
[58] Field of Search .................... 564/65, 55; 528/422; 560/24

[56] References Cited

FOREIGN PATENT DOCUMENTS 1275702  5/1972  United Kingdom .

OTHER PUBLICATIONS

Kiyoshi Kondo et al, "Selenium–Catalyzed Synthesis of Urea Derivatives from Amino Acid Esters, Carbon Monoxide, and Oxygen", 1979, Synthesis, pp. 735–736.
Noboru Sonoda et al, "A New Synthesis of Ureas. The Reaction of Ammonia or Aliphatic Amines with Carbon Monoxide in the Presence of Selenium", 1971, Journal of the American Chemical Society, p. 6344.
Chemistry Letters, pp. 373–374, 1972.

*Primary Examiner*—Harold D. Anderson
*Attorney, Agent, or Firm*—Spencer & Frank

[57] ABSTRACT

Process for the catalytic synthesis of nitrogen-containing organic compounds, comprising the reaction of carbon monoxide with at least one amino compound in a reaction mixture containing a catalyst based on selenium and a substituted pyridine. The process is particularly suitable for the synthesis of ureas and of their polymers.

6 Claims, No Drawings

CATALYTIC SYNTHESIS OF UREA FROM CARBON MONOXIDE AND AMINE COMPOUND

FIELD OF THE INVENTION

The present invention relates to a process for the catalytic synthesis of nitrogen-containing organic compounds which contain at least one >N—CO group in their molecule. It relates more particularly to a process for the catalytic synthesis of ureas and of their polymers.

BACKGROUND OF THE INVENTION

It is known to manufacture nitrogen-containing organic compounds, such as ureas and carbamates, by methods of synthesis which require the catalytic insertion of carbon monoxide into the >NH— bonds of compounds containing at least one amino group, in the presence of metal catalysts, and in a liquid reaction medium containing a nitrogen-containing organic base.

Thus, Patent GB-A No. 1,275,702 (ASAHI KASEI and CHIYODA KAKO) discloses a process for the manufacture of ureas or of urea derivatives by reaction of ammonia or of an amine with carbon monoxide in the presence of selenium. The reaction is preferably carried out in the presence of oxygen and of a basic solvent such as triethylamine or a tertiary amine. Other basic solvents, such as tetrahydrofuran and pyridine, have also been used to carry out this reaction (Journal of American Chemical Society, 1971, volume 93, No. 23, page 6344).

K. Kondo and colleagues have described the synthesis of carbamides by reaction of esters of aminoacids with carbon monoxide and oxygen in the presence of a catalyst comprising selenium and triethylamine (Synthesis, 1979, No. 9, pages 735–736).

The manufacture of carbamates from amines, alcohols, carbon monoxide and oxygen has been described by K. Kondo and colleagues in Chemistry Letters, 1972, No. 5, pages 373–374. This document discloses the use, in this reaction, of primary aromatic amines, selenium and triethylamine.

These methods of synthesis of the abovementioned nitrogen-containing organic compounds, however, suffer from certain disadvantages. The productivity of the reactors is low because the reactions are excessively slow, in spite of the use of high pressures and high temperatures, or the yield of the reactions is mediocre, or the selectivity in respect of the desired final product is poor and a large quantity of undesirable byproducts is obtained.

SUMMARY OF THE INVENTION

An object of the present invention is to overcome the disadvantages of the known processes and to provide a process which gives, together with good productivity, a high selectivity in respect of the nitrogen-containing organic compound of the desired structure.

A more particular object of the invention is to provide a process which gives, with good yield, derivatives and polymers of ureas whose properties are easily controllable, in particular high molecular weight polymers of ureas.

The invention relates, to this effect, to a process for the catalytic synthesis of nitrogen-containing organic compounds containing at least one >N—CO—group in their molecule, which comprises the reaction of carbon monoxide with an amino compound in a reaction mixture containing a catalyst based on selenium and a liquid organic medium, according to which process the liquid organic medium contains a substituted pyridine.

By amino compounds employed in the process according to the invention, there is to be understood the class of compounds consisting of ammonia and of all the compounds containing at least one amine group wherein the nitrogen is monosubstituted or disubstituted, that is to say containing a primary or secondary amino group.

DETAILED DESCRIPTION OF THE INVENTION

The compounds containing at least one primary or secondary amino group, employed in the process according to the invention, generally correspond to one of the following formulae:

and

In the formulae (I) and (III) representing the monoamino compounds respectively containing a primary or secondary amino group, R, $R^2$ and $R^3$ represent any monovalent organic radicals. They are generally chosen from among the radicals containing from 1 to 20 carbon atoms. These radicals can be saturated or unsaturated and have branched, straight or cyclic hydrocarbon chains. They can be aliphatic radicals, in particular alkyl or alkenyl radicals comprising from 1 to 18 carbon atoms cycloaliphatic radicals, in particular cycloalkyl radicals comprising from 5 to 14 carbon atoms, arylaliphatic radicals, in particular aralkyl radicals comprising from 7 to 14 carbon atoms monocyclic aromatic radicals, in particular aryl and alkylaryl radicals containing from 6 to 14 carbon atoms, and polycyclic aromatic radicals of which the nuclei can be fused or joined by simple valency bonds, in particular aromatic radicals having two benzene nuclei.

The linear or cyclic hydrocarbon chains of the radicals R, $R^2$ and $R^3$ can be interrupted by hetero atoms different from carbon or by any electron donor groups. The hetero atoms can be atoms of oxygen, sulphur and nitrogen, for example. The electron donor groups can be, for example, sulphoxide, sulphone, amino, amide, carbonyl, carboxyl and azo groups.

The radicals R, $R^2$ and $R^3$ can be substituted by one or more substituents of any desired type.

These substituents can, for example, themselves be organic radicals with hydrocarbon chains of the same nature as those defined above. They can also be any desired functional groups, for example halogen, alkoxy, aryloxy, carboxy, hydroxy, nitro, nitroso, keto and oxo groups.

In the formula (III), the radicals $R^2$ and $R^3$ can be identical or different. They can also be doubled back onto themselves to form a ring in which the secondary amino group is included.

In the formula (II) representing the diamino compounds containing two amino groups, $R^1$ represents any desired divalent organic radical. This radical, except for its divalent character, corresponds in all respects to the definitions and limitations set out above in relation to the radicals R, $R^2$ and $R^3$. If it is an aliphatic radical, it can thus be, in particular, an alkylene or alkenylene radical comprising from 1 to 18 carbon atoms. If it is a cycloaliphatic radical, it can in particular be a cycloalkylene radical comprising from 5 to 14 carbon atoms and, in the case where it is a monocyclic aromatic radical, it can in particular be an arylene or alkylarylene radical containing from 6 to 14 carbon atoms.

Finally, in formula (IV), $R^4$ and $R^5$, which may be identical or different, also each represent a divalent organic radical which is generally an aliphatic radical and, in particular, an alkylene radical comprising from 1 to 10 carbon atoms.

Particular and non-limiting examples of amino compounds corresponding to one of the above formulae are:

Compounds containing only one primary amino group (formula (I)), such as the aliphatic primary monoamines, for example methylamine, ethylamine, n-butylamine and n-octylamine; cycloaliphatic primary monoamines such as, for example, cyclohexylamine; monocyclic aromatic primary monoamines, such as, for example, aniline and the o-, m- and p-toluidines; alkylaromatic primary monoamines such as, for example, benzylamine; polycyclic aromatic primary monoamines such as, for example, the α- and β-naphthylamines and 3-aminopyrene; heterocyclic primary monoamines such as, for example, β-aminopyridine and 2-aminothiazole; the alpha-monoamino derivatives of aliphatic carboxylic acids and their esters, such as, for example, glycine, alanine, serine and their ethyl esters; the monoamino derivatives of aromatic carboxylic acids, such as, for example, proline and p-aminobenzoic acid, the monoamino derivatives of alcohols and phenols such as, for example, monoethanolamine and p-aminophenol; the monoamino derivatives of aldehydes, such as, for example, p-aminobenzaldehyde; and the monoamino derivatives of quinones, such as, for example, α- and β-aminoanthraquinones, 4-amino-1,2-naphthaquinone and 2-amino-1,4-napthaquinone.

Compounds which contain only one secondary amino group (formula (III)) such as the aliphatic secondary monoamines, for example dimethylamine, diethylamine and piperidine; the aromatic secondary monoamines, such as, for example, the N-substituted derivatives of aniline, in particular the N-alkyl-substituted derivatives of the latter, diphenylamine and pyrrole.

The compounds containing two primary amino groups (formula (II)) as the aliphatic primary diamines, for example ethylenediamine and 1,6-hexamethylenediamine; cycloaliphatic primary diamines, such as, for example, 4,4'-diaminodicyclohexylmethane; aromatic primary diamines, such as, for example, 4,4'-methylenedianiline 4,4'-diaminostilbene, p-phenylenediamine, p,'-diaminodiphenyl and 2,4- and 2,6-toluenediamine; alkylaromatic primary diamines such as, for example, m-xylylenediamine; heterocyclic primary diamines, such as, for example, 2,6-diaminopyridine; the diamino derivatives of terpene hydrocarbons, such as, for example, 1,8-diamino-p-methane; the diamino derivatives of aliphatic carboxylic acids, such as, for example, lysine; the diamino derivatives of aromatic carboxylic acids, such as, for example, 3,5-diaminobenzoic acid; the diamino derivatives of sulphones, such as, for example, 4,4'-diaminodicyclohexyl- and 4,4'-diaminodiphenyl-sulphone; the diamino derivatives of ethers, such as, for example, 4,4'-diaminodiphenyl ether; the diamino derivatives of ketones, such as, for example 4,4'-diaminobenzophenone; and the diamino derivatives of quinones, such as, for example, 2,6-aminoanthraquinone.

The compounds containing two secondary amino groups (formula (IV)), such as the aliphatic secondary diamines, for example piperazine.

The choice of the amino compound to be employed in the process according to the invention is determined by the nature of the nitrogen-containing organic compound which it is desired to obtain. Furthermore, the nature of the nitrogen-containing organic compound which it is desired to obtain may, in a known manner, require the possible presence of other reagents than the amino compound and carbon monoxide in the reaction mixture.

Thus, the process according to the invention in particular makes it possible to manufacture:

Ureas, from ammonia or monoamino compounds represented, for example, by one of formulae (I) or (II) above, carbon monoxide and oxygen, for example in accordance with one of the following equations:

$$2NH_3 + CO + \tfrac{1}{2}O_2 \rightarrow NH_2-CO-NH_2 + H_2O \quad (A)$$

$$2RNH_2 + CO + \tfrac{1}{2}O_2 \rightarrow R-NH-CO-NH-R + H_2O \quad (B)$$

$$2R^2-NH-R^3 + CO + \tfrac{1}{2}O_2 \rightarrow (R^2R^3N)_2CO + H_2O \quad (C)$$

in which R, $R^2$ and $R^3$ have the meanings given above, R being preferably chosen from among aliphatic and aromatic radicals and $R^2$ and $R^3$ from among aromatic radicals, more especially respectively from among alkyl radicals comprising from 1 to 10 carbon atoms, for example the methyl, ethyl and butyl radicals, and from among aryl radicals, for example a phenyl radical;

Polyureas from diamino compounds represented, for example, by the above formula (II), carbon monoxide and oxygen, for example in accordance with the following equation:

$$(n+1)(NH_2-R^1-NH_2) + nCO + \tfrac{n}{2}O_2 \longrightarrow \quad (D)$$

$$NH_2\text{-}(R^1-NHCONH)_nR^1NH_2 + nH_2O$$

in which $R^1$ has the meaning mentioned above and is preferably chosen from among aliphatic and aromatic radicals, more particularly respectively from among alkylene or alkenylene radicals comprising from 2 to 10 carbon atoms and from among arylene or alkylarylene radicals containing from 6 to 14 carbon atoms, and in which n is generally between 1 and 5,000, preferably between 2 and 1,000;

Carbamates from monoamino and diamino compounds represented, for example, by the formulae (I) and (II) above, alcohols or thiols, carbon monoxide and oxygen, for example in accordance with one of the following equations:

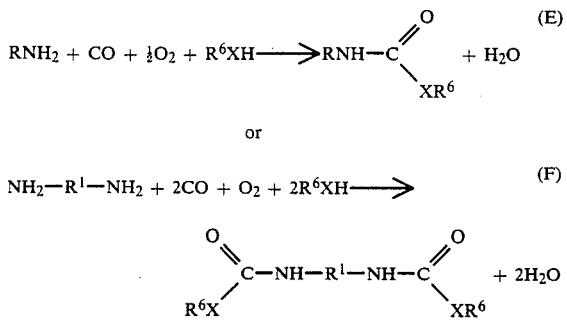

in which R and R¹ have the meanings mentioned above and are preferably aromatic radicals, for example a phenyl radical, R⁶ is an aliphatic radical, preferably a linear or branched alkyl radical comprising from 1 to 10 carbon atoms, for example a methyl, ethyl or butyl radical, and X represents an oxygen or sulphur atom (in the latter case, the compound R⁶XH is a thiol and the nitrogen-containing organic compound obtained is the corresponding thiocarbamate);

Urethane oligomers from diamino compounds represented, for example, by formula (II) above, carbon monoxide, oxygen and diols or dithiols, for example in accordance with the following equation:

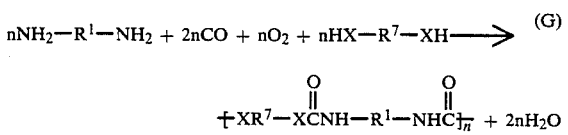

in which R¹ has the meaning mentioned above and is preferably an aromatic radical, for example a phenyl radical, R⁷ is a divalent aliphatic radical, preferably an alkylene radical comprising from 1 to 10 carbon atoms, for example a methylene radical, n is an integer which is generally between 1 and 100, preferably between 2 and 10, and X represents an oxygen or sulphur atom;

Amides from monoamino and diamino compounds represented, for example, by one of the formulae (I) to (IV) above and carbon monoxide, for example in accordance with one of the following equations:

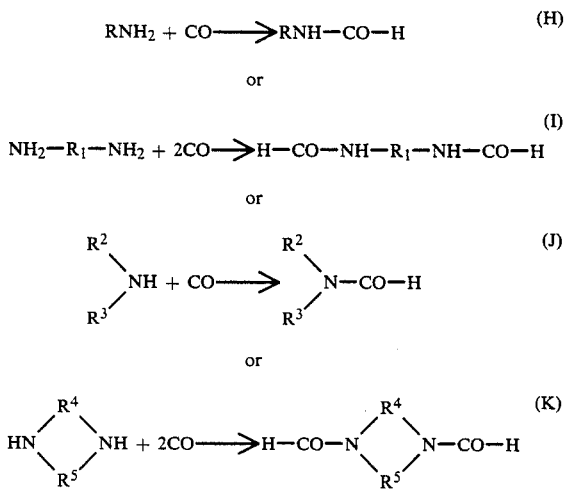

in which R, R¹, R², R³, R⁴ and R⁵ have the meanings mentioned above and are preferably aliphatic radicals, more especially alkyl or alkylene radicals comprising from 1 to 10 carbon atoms, for example a methyl, ethyl or butyl radical and a methylene radical.

The process according to the invention is particularly suitable for the synthesis of ureas in accordance with equations (A) to (C) and of urea polymers in accordance with equation (D) because it allows the preparation, under particularly mild working conditions, of, on the one hand, ureas at an unexpected reaction rate and with an unexpected selectivity and, on the other hand, of polyureas of very high molecular weight.

By way of examples of amino compounds very particularly preferred for the manufacture of urea polymers in accordance with equation (D), there may be mentioned 4,4'-methylenedianiline, 2,4-toluenediamine, 1,6-hexamethylenediamine and p- and m-phenylenediamines. It is possible to use a single diamino compound in order to obtain homopolymers or a plurality of diamino compounds in order to obtain copolymers.

The general working conditions under which the catalytic synthesis of the nitrogen-containing organic compounds according to the invention is carried out are known (see the documents cited in the introduction to the description, the contents of which are incorporated by reference) and can vary to a great extent depending on the nature of the compound which it is desired to manufacture.

As mentioned above, the synthesis is carried out in a reaction mixture containing a selenium-based catalyst. The selenium present in the catalyst can be in the form of metallic selenium, amorphous selenium or a compound capable of producing selenium under the synthesis conditions. Preferably, the selenium is present in the metallic form.

The catalyst concentration in the reaction mixture can vary widely. In general it does not exceed the amount which can be dissolved in the liquid organic medium present in the mixture, under the conditions under which the synthesis is carried out. Expressed in moles of selenium contained in the catalyst per liter of organic medium, it is generally between 0.005 and 0.5 mole/l, preferably between 0.01 and 0.2 mole/l. The best results have been recorded for catalyst concentrations of between 0.02 and 0.15 mole of selenium per liter.

The reaction mixture in which the synthesis of the nitrogen-containing organic compound is carried out contains a liquid organic medium. This liquid organic medium is generally a medium which is inert towards the reactants employed and capable of dissolving the amino compound used. This liquid organic medium can contain an aliphatic alcohol such as, for example, ethanol, a ketone such as, for example, acetone and methyl ethyl ketone, an ether, such as, for example, dioxane and tetrahydrofuran, an aliphatic hydrocarbon such as, for example, hexane and cyclohexane, an aromatic hydrocarbon such as, for example, benzene, an N,N-disubstituted amide such as, for example, dimethylformamide and dimethylacetamide, an ester such as, for example, ethyl acetate or a tertiary aliphatic amine such as, for example, triethylamine.

The liquid organic medium can contain only one of the compounds mentioned above, or a mixture of these compounds.

According to the invention, the liquid organic medium contains a substituted pyridine, optionally together with at least one of the compounds enumerated above. It has in fact been found, surprisingly, that the presence of a substituted pyridine in the liquid organic medium leads to a number of results which are advantageous and were not foreseeable a priori. Thus, its presence permits the synthesis of ureas, carbamates, thiocarbamates, urethane oligomers and amides in accordance with one of equations (A) to (C) and (E) to (K) above, at high reaction rates, with excellent selectivity and a very high yield, under gentle temperature and pressure conditions. Moreover, the presence of a substituted pyridine in the liquid organic medium surprisingly permits the synthesis of urea polymers of very high molecular weight, under very moderate temperature and pressure conditions. Thus, by virtue of the process of the invention, it has been possible to obtain straight chain urea polymers whose weight-average molecular weight and number-average molecular weight (measured in a conventional manner by gel permeation chromatography) respectively are as high as $300 \times 10^3$ and $70 \times 10^3$.

The term substituted pyridine is intended to denote all pyridine derivatives which carry at least one substituent of any desired type on the aromatic nucleus; these derivatives can be halogenated derivatives such as, for example, 2-chloropyridine, 3-chloropyridine and 2,5-chloropyridine, alkoxylated derivatives such as, for example, 3-methoxypyridine and 4-methoxypyridine, and alkylated derivatives such as, for example, picolines, lutidines, collidines, ethylpyridines and propylpyridines. It is preferred to use dialkylated derivatives of pyridine, and among these the lutidines (2,3-, 2,4-, 2,5-, 2,6-, 3,4-, 3,5- and 3,6-), with 2,4-lutidine (2,4-dimethylpyridine) being very particularly preferred.

Where it is desired to ensure maximum solubility of the nitrogen-containing organic compound synthesized according to the process of the invention, it is preferred that the liquid organic medium should be a medium as polar and as basic as possible; in this case it is preferred that the liquid organic medium should essentially consist of the mixture of a tertiary aliphatic amine or of an N,N-disubstituted aliphatic amide with substituted pyridine. Good results, especially in the case of the synthesis of high molecular weight polyureas, have been obtained in a liquid organic medium comprising a mixture of dimethylacetamide or dimethylformamide and 2,4-lutidine, in molar ratios of the amide to the lutidine which are generally between 1/10 and 10/1 and preferably between 1/1 and 4/1.

According to the invention, the liquid organic medium can furthermore contain an alkali metal halide, preferably a lithium halide, more especially a chloride or a bromide of this metal, which permits increasing the solubility of the nitrogen-containing organic compound in the reaction mixture; this proves particularly advantageous in the case of the synthesis of high molecular weight polyureas. Usually, the lithium halide is present in the liquid organic medium in a proportion of 0.1 to 10 moles per mole of substituted pyridine, preferably in a proportion of 1 to 5 moles per mole. The best results have been obtained when the liquid organic medium contains a mixture of dimethylacetamide and 2,4-lutidine to which about 1 mole of lithium halide has been added per mole of 2,4-lutidine.

The concentration of the amino compound in the reaction mixture can vary within wide limits. In general, the upper limit of concentration of the amino compound in the reaction mixture is imposed by the viscosity imparted to the latter. It is usually between 0.01 and 5 moles of amino compound per liter of the volume of reaction mixture, preferably between 0.1 and 1 mole per liter.

Other reactants necessary for the synthesis of the desired nitrogen-containing organic compound are introduced into the reaction mixture in molar ratios, with respect to the amino compound, which are of the order of magnitude required for the equation leading to the said organic compound.

The sequence of introduction of the reactants into the reaction mixture is optional. In general, it is preferred to introduce the carbon monoxide—in the pure form or in the form of a gas in which it is present—into the reaction mixture into which the amino compound, the catalyst and the optional other reactants have been introduced beforehand, and to introduce oxygen slowly simultaneously with or, preferably, subsequently to the introduction of carbon monoxide.

The temperature and pressure at which the reaction is carried out can vary within very wide limits. However, the process of the invention permits operation under temperature and pressure conditions below those used in the synthesis processes of the prior art. They are chosen in accordance with the nature of the nitrogen-containing organic compound which it is desired to synthesize, and in such a way as not to exceed the decomposition temperature of the reaction mixture. The temperature is usually below 250° C. It is generally between 150° and 200° C. in the case of the syntheses represented by equations (E) and (K). Surprisingly, the process according to the invention makes it possible to carry out the syntheses represented by equations (A) to (D), in particular the synthesis of the polyureas according to equation (D), at remarkably low temperatures, which are usually between 0° and 70° C. and preferably between 20° and 40° C.

The total pressure is usually below 10 MPa and is preferably between 2 and 5 MPa.

The reaction time depends on the nature of the nitrogen-containing organic compound which it is desired to synthesize. It can vary from a few minutes to several tens of hours. By virtue of the process according to the invention, the reaction rates are generally very high, for example permitting the synthesis of carbamates and of ureas in a few (20 to 30) minutes. Polyureas of very high intrinsic viscosity (up to about 0.43 l/g measured at 25° C. in dimethylformamide containing a molar concentration of LiBr), corresponding to values of the weight-average and number-average molecular weights mentioned above, can be obtained in a few (2 to 3) hours.

The process according to the invention can be carried out continuously or discontinuously in a single reactor or in reactors arranged in parallel or in series. Any apparatus suitable for liquid reaction mixtures can be used to carry out the process according to the invention.

The examples which follow illustrate the invention without restricting its scope.

EXAMPLE 1

0.63 g of metallic selenium (8 millimoles) and 90 ml of a solution C are introduced into an 0.3 liter stainless steel autoclave heated by means of an electric oven and equipped with a stirrer, a coil for the circulation of cooling water, a thermocouple used to read and regulate the temperature and a dip tube for the introduction of gases.

Solution C is prepared as follows:

(a) 1 liter of a solution A of dimethylacetamide which is 2.12 molar in respect of lithium chloride is prepared beforehand;

(b) thereafter, one liter of solution B containing a mixture of solution A and 2,4-dimethylpyridine (2,4-lutidine) is prepared, so that solution B is 2.39 molar in respect of 2,4-lutidine;

(c) finally, 1 liter of solution C is prepared by dissolving 115.7 g of 4,4'-methylenedianiline (MDA) in solution B, so that solution C is 0.58 molar in respect of MDA.

After the autoclave has been closed and brought to atmospheric pressure and the contents have been brought to 30° C., carbon monoxide is introduced in the amount required to give a molar ratio of CO/MDA=3.

24 minutes after the start of the introduction of the CO, oxygen is introduced at a rate of 0.2 liter/min and in the amount necessary to achieve a molar ratio of $O_2$/MDA=1.5.

The reaction is continued under autogenous pressure for 2 hours while maintaining the temperature at 30° C.; the autoclave is then brought to ambient temperature and is degassed, and its contents are collected.

After having removed the selenium by bubbling air through the batch and filtering it, the reaction mixture is put into 10 times its volume of methanol to precipitate the polymer formed.

The polymer is recovered by filtration, washed with methanol and acetone and then dried at 70° C. The yield is practically quantitative.

The urea polymer obtained is composed of linear macromolecular chains, as revealed by NMR ($^{13}C$) examination.

The intrinsic viscosity of the polymer measured at 25° C. in dimethylformamide which is molar in respect of lithium bromide is 0.382 l/g.

COMPARATIVE EXAMPLES 2 and 3

These examples are given by way of comparison.

The working method of Example 1 is repeated exactly, except that in the preparation of solution B the 2,4-dimethylpyridine is replaced by an equimolar amount of triethylamine (Example 2) or of pyridine (Example 3).

The intrinsic viscosities of the polyureas obtained, measured as indicated in Example 1, are shown in the table below:

TABLE

| | Nature of the base | Intrinsic viscosity of the polymer (l/g) |
|---|---|---|
| Example 2 | triethylamine | 0.033 |
| Example 3 | pyridine | 0.035 |

Comparison of these results with those of Example 1 shows that the presence of 2,4-lutidine in the liquid organic medium makes it possible, all other conditions being equal, to obtain polyureas of markedly higher mean molecular weight.

EXAMPLE 4

In an autoclave such as that used in Example 1, 10 ml of aniline (109.7 millimoles) are added to a solution containing 75 ml of 2,4-lutidine, 35 ml of methanol and 0.3 g of selenium. When a temperature of 170° C. has been reached, carbon monoxide, at a partial pressure of 4 MPa, and oxygen, at a partial pressure of 1.5 MPa, are successively introduced. The total pressure in the autoclave is kept constant throughout the duration of the reaction by leaving the oxygen gas cylinder open. After 9 minutes at 170° C., analysis shows that 106.4 millimoles have been consumed (degree of conversion 97%), to form 97.9 millimoles of methyl N-phenylcarbamate (92% selectivity).

COMPARATIVE EXAMPLE 5

This example is given by way of comparison. The procedure followed is as in Example 4 except that the 2,4-lutidine is replaced by an equivalent volume of pyridine. After 9 minutes' reaction at 170° C., the degree of conversion was 96% and the selectivity in respect of carbamate only 63%.

EXAMPLE 6

85 ml of aniline, 1.16 liters of dimethylformamide, 0.44 liter of 2,4-lutidine and 2.8 g of selenium are introduced into a 5 liter autoclave similar to that used in Example 1.

The autoclave is closed and the mixture is brought to 30° C. Carbon monoxide is introduced in the amount necessary to give a molar ratio of CO/aniline=3. 24 minutes after the introduction of the carbon monoxide, oxygen is introduced at a rate of 0.6 liter/min, and in the amount necessary to give a molar ratio of $O_2$/aniline=1.5.

The reaction is continued under autogenous pressure for 1 hour while keeping the temperature at 30° C. The autoclave is then degassed and its contents collected. Analysis of the reaction mixture by gas phase chromatography shows complete conversion of the aniline to diphenyl urea.

EXAMPLE 7

0.5 g of selenium oxide ($SeO_2$), 75 ml of 2,4-lutidine and 7.66 g of ammonia are introduced into a 0.5 l autoclave similar to that used in Example 1. The reaction medium is heated until its temperature reaches 30° C.

11.09 liters of carbon monoxide are then introduced, followed by 7.39 liters of oxygen, at a flow rate of 0.39 liter/min. 30 minutes after the introduction of oxygen, the autoclave is cooled and degassed.

The yield of synthetized urea is about 86%.

COMPARATIVE EXAMPLE 8

This example is given by way of comparison.

The procedure detailed in Example 7 is reproduced except that the 2,4-lutidine is replaced by the same volume of methanol.

The yield of synthetized urea is only about 5%.

We claim:

1. Process for the catalytic synthesis of nitrogen-containing organic compounds containing at least one >N—CO— group in their molecule, which comprises reacting carbon monoxide with at least one amine compound in a reaction mixture containing a catalyst based on selenium and a liquid organic medium, characterized in that the liquid organic medium contains a substituted pyridine.

2. Process according to claim 1, applied to the catalytic synthesis of ureas, characterized in that the amino compound is chosen from among ammonia or monoamino compounds and in that the reaction mixture furthermore contains elemental oxygen to act as an oxidizing agent.

3. Process according to claim 1, characterized in that the liquid organic medium contains an N,N-disubstituted aliphatic amide to act as a solvent in addition to the substituted pyridine.

4. Process according to claim 3, characterized in that the liquid organic medium furthermore contains a lithium halide to increase the solubility of the reactants.

5. Process according to claim 1, characterized in that the substituted pyridine is an alkylated derivative of pyridine.

6. Process according to claim 5, characterized in that the substituted pyridine is 2,4-lutidine.

* * * * *